United States Patent
Nguyen

(10) Patent No.: US 11,178,512 B2
(45) Date of Patent: Nov. 16, 2021

(54) PORTABLE VAPORIZER SYSTEM AND METHOD

(71) Applicant: Tommy Nguyen, Kitchener (CA)

(72) Inventor: Tommy Nguyen, Kitchener (CA)

( * ) Notice: Subject to any disclaimer, the term of this patent is extended or adjusted under 35 U.S.C. 154(b) by 149 days.

(21) Appl. No.: 16/680,984

(22) Filed: Nov. 12, 2019

(65) Prior Publication Data

US 2020/0337383 A1 Oct. 29, 2020

Related U.S. Application Data

(63) Continuation of application No. 29/688,875, filed on Apr. 25, 2019.

(30) Foreign Application Priority Data

May 1, 2019 (CA) .......................................... 187269
Jul. 18, 2019 (EP) ................................... 006635595

(51) Int. Cl.
| | | |
|---|---|---|
| A24F 11/00 | (2006.01) | |
| H04W 4/029 | (2018.01) | |
| H04W 4/20 | (2018.01) | |
| G08B 7/06 | (2006.01) | |
| H04W 4/38 | (2018.01) | |
| H02J 7/00 | (2006.01) | |
| G16H 40/67 | (2018.01) | |
| G06Q 30/06 | (2012.01) | |

(52) U.S. Cl.
CPC ........ *H04W 4/029* (2018.02); *G06Q 30/0633* (2013.01); *G08B 7/06* (2013.01); *G16H 40/67* (2018.01); *H02J 7/0045* (2013.01); *H02J 7/0063* (2013.01); *H04W 4/20* (2013.01); *H04W 4/38* (2018.02)

(58) Field of Classification Search
CPC .................................. H04W 4/029; G08B 7/06
USPC ................ 131/328–329, 270, 273, 361, 194; 320/107–108, 114–115; 340/517, 521, 340/540, 541
See application file for complete search history.

(56) References Cited

U.S. PATENT DOCUMENTS

| | | | |
|---|---|---|---|
| 8,499,766 B1 * | 8/2013 | Newton | ................... A24F 40/40 131/273 |
| D751,249 S | 3/2016 | Chen | |
| (Continued) | | | |

FOREIGN PATENT DOCUMENTS

EP        2875740 A3     5/2016

*Primary Examiner* — Tai T Nguyen

(74) *Attorney, Agent, or Firm* — Argus Intellectual Enterprise; Jordan Sworen; Daniel Enea

(57) ABSTRACT

A portable vaporizer system and method are provided. The portable vaporizer system includes a housing having an airflow channel connecting an air inlet to a vapor outlet through a mouthpiece disposed at a first end of the housing. A fluid chamber within the housing can store fluid to be vaporized and is operably connected to an atomizer within the housing, between the air inlet and the vapor outlet. A power control is disposed at a base of the housing and can selectively adjust voltage supplied from a power source to the atomizer for controlling a fluid temperature during the vaporizing process. A sensor is disposed within the housing for detecting fluid levels, power usage, flow rates, and the like. The information detected by the sensor is stored as user data and transmitted to a remote electronic device, wherein a graphical user interface (GUI) displays the user data.

16 Claims, 3 Drawing Sheets

(56) References Cited

U.S. PATENT DOCUMENTS

| | | | |
|---|---|---|---|
| 9,282,772 B2 | 3/2016 | Tucker et al. | |
| D759,297 S | 6/2016 | Liu | |
| D776,869 S | 1/2017 | Heidl | |
| D800,379 S | 10/2017 | Fang | |
| 2013/0152922 A1 | 6/2013 | Benassayag et al. | |
| 2014/0041655 A1 | 2/2014 | Barron et al. | |
| 2015/0122252 A1 | 5/2015 | Frija | |
| 2015/0136158 A1* | 5/2015 | Stevens | H02J 7/0091 131/329 |
| 2015/0166029 A1* | 6/2015 | Yamasaki | B60T 7/042 303/14 |
| 2015/0333561 A1* | 11/2015 | Alarcon | H02J 50/40 131/329 |
| 2015/0335074 A1* | 11/2015 | Leung | A61M 15/06 131/328 |
| 2018/0020734 A1 | 1/2018 | Angstead et al. | |
| 2018/0092406 A1 | 4/2018 | Monsees et al. | |

* cited by examiner

PORTABLE VAPORIZER SYSTEM AND METHOD

CROSS REFERENCE TO RELATED APPLICATION

This application claims the benefit of U.S. Design patent application Ser. No. 29/688,875 filed on Apr. 25, 2019, CA Application No. 187269 filed on May 1, 2019, and EU Application No. 006635595 filed on Jul. 18, 2019; the above identified patent applications are herein incorporated by reference in its entirety.

BACKGROUND OF THE INVENTION

The present invention relates to vaporization devices. More specifically, the present invention relates to a portable vaporizer system and method configured to detect and store user data and transmit the user data to remote electronic devices.

Vaporizer devices, commonly known as vape pens, and electronic cigarettes are used to vaporize plant substances for inhalation. Many vape pen users and e-cigarette smokers enjoy the technology associated with existing vaporization devices. However, existing vaporization devices lack customizability and the functionality to anticipate user needs, such as automatically ordering refills when fluid levels are low or providing power charging and usage status to an application on a remote electronic device, such as a smartphone or tablet. Further, vape pens and e-cigarettes are designed to be discrete, which can lead to the device being easily lost or misplaced. Therefore, there exists a need for a portable vaporization system configured to allow a user to track its location and well as receive alerts in order to locate a lost device.

Other people use existing vaporization devices to quit smoking. However, existing devices lack convenient safety and health features to assist a person to quit smoking or vape in the most responsible manner. Therefore, there exists a need for a portable vaporization system configured to track and store usage data, wherein that usage data can be later reviewed by the user and a healthcare professional. Further, there is a need for a device to measure flow rate in order to alert a user if he or she is over-inhaling.

In light of the devices disclosed in the known art, it is submitted that the present invention substantially diverges in design elements and methods from the known art and consequently it is clear that there is a need in the art for an improvement for portable vaporizer systems and methods. In this regard the instant invention substantially fulfills these needs.

SUMMARY OF THE INVENTION

In view of the foregoing disadvantages inherent in the known types of portable vaporizer systems and methods now present in the known art, the present invention provides a new portable vaporizer system and method wherein the same can be utilized for tracking user data associated with usage and current status of the system.

It is one objective of the present invention to provide a portable vaporizer system comprising a housing having a first end and a second end extending between a longitudinal axis, an air inlet, and a vapor outlet. An airflow channel in the housing connects the air inlet to the vapor outlet and an atomizer is disposed in the housing between the air inlet and the vapor outlet. A fluid chamber is operably connected to the atomizer.

It is another objective of the present invention to provide a portable vaporizer system having at least one sensor configured to detect user data, such as fluid levels, flow rates, power usage, and a wireless transmitter configured to transmit the user data to a remote electronic device configured to display the user data on a GUI.

It is another objective of the present invention to provide a portable vaporizer system comprising a power control disposed at a base of the housing and operably connected to the atomizer in order to selectively control the power supply thereto.

It is yet another objective of the present invention to provide a method for using a portable vaporizer comprising the steps of detecting user data, such as flow rates, fluid levels, and power usage, sending the user data to a remote electronic device and causing fluid refills to be reordered automatically.

It is yet another objective of the present invention to provide a method for using a portable vaporizer comprising the steps of alerting a user via illumination of a light source and audible sound when prompted by remote actuation in order to locate the portable vaporizer.

It is therefore an object of the present invention to provide a new and improved portable vaporizer system and method that has all of the advantages of the known art and none of the disadvantages.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings.

Reference will now be made in detail to the exemplary embodiment (s) of the invention. References to "one embodiment," "at least one embodiment," "an embodiment," "one example," "an example," "for example," and so on indicate that the embodiment(s) or example(s) may include a feature, structure, characteristic, property, element, or limitation but that not every embodiment or example necessarily includes that feature, structure, characteristic, property, element, or limitation. Further, repeated use of the phrase "in an embodiment" does not necessarily refer to the same embodiment. Additionally, "vape pen," "vaporization device," and "vaporization system" may be used interchangeably and refer to the present invention.

As used herein, "computer-readable medium" or "memory" excludes any transitory signals, but includes any non-transitory data storage circuitry, e.g., buffers, cache, and queues, within transceivers of transitory signals. As used herein, "logic" refers to (i) logic implemented as computer instructions and/or data within one or more computer processes and/or (ii) logic implemented in electronic circuitry. References to "display" or "display screen" include any electronic device, such as a computer or tablet having an interactive touchscreen.

DETAILED DESCRIPTION OF THE INVENTION

Reference is made herein to the attached drawings. For the purposes of presenting a brief and clear description of the present invention, the preferred embodiment will be discussed as used for detecting and transmitting user data to a remote electronic device. The figures are intended for representative purposes only and should not be considered to be limiting in any respect.

Figure 1:
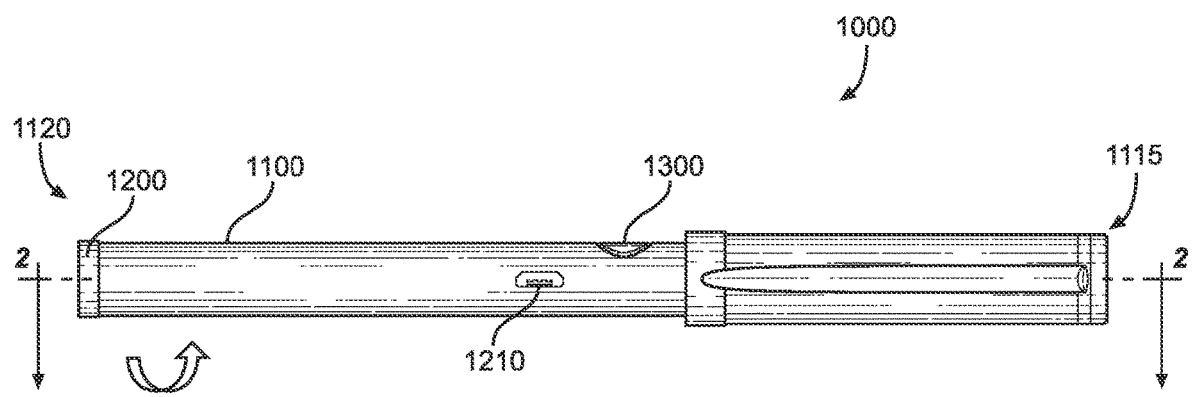
FIG. 1 shows a perspective view of an embodiment of the portable vaporizer system.
Figure 2:
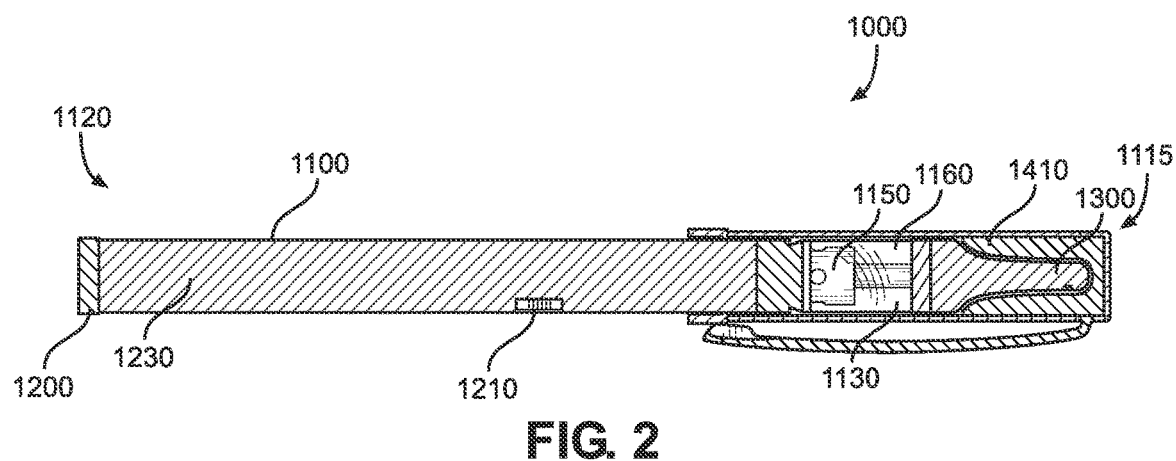
FIG. 2 shows a cross sectional view of an embodiment of the portable vaporizer system, taken along line 2-2 of FIG. 1.

Referring now to FIGS. 1 and 2, there is shown a perspective view of an embodiment of the portable vaporizer system and a cross sectional view of an embodiment of the portable vaporizer system, taken along line 2-2 of FIG. 1, respectively. The portable vaporizer system 1000 comprises a housing 1100 having a first end 1115 and a second end 1120 extending between a longitudinal axis. In the illustrated embodiment, the housing 1100 is cylindrical. However, in alternate embodiments, the housing comprises any suitable shape. An airflow channel 1130 extends through the first end 1115 of the housing 1100 and connects an air inlet to a vapor outlet therein. In the illustrated embodiment, the vapor outlet is disposed on a mouthpiece 1300 extending from the housing 1100. The air inlet is configured to receive airflow from the exterior of the housing 1100 and the vapor outlet is adapted to discharge the airflow therefrom.

An atomizer 1150 is disposed within in the housing 1100 between the air inlet and the vapor outlet. The atomizer 1150 comprises a heating element and is configured to vaporize fluid disposed in a fluid chamber 1160. In the illustrated embodiment, the fluid chamber 1160 is operably connected to the atomizer 1150 and configured to heat fluid from the fluid chamber 1160 in order to vaporize the fluid. In one embodiment, the fluid chamber 1160 is a removable cartridge that is interchangeable with other similar cartridges. Once the fluid is vaporized, the vapors are discharged through the vapor outlet. In the illustrated embodiment, the fluid chamber 1160 is composed of transparent glass to allow the fluid levels disposed therein to be view by a user. In alternate embodiments, the fluid chamber is composed of any suitable material configured to retain fluid therein.

In the illustrated embodiment, a power control 1200 is disposed at a base of the second end 1120 of the housing 1100 and configured to selectively adjust voltage supplied from a power source to the atomizer 1150 for controlling a liquid temperature during the vaporizing process. In the illustrated embodiment, the power control 1200 is a rotatable dial configured to rotate around the longitudinal axis of the housing 1100. However, in alternate embodiments, the power control 1200 is any suitable actuation control, such as a button or toggle. The rotatable dial provides for convenient access to the power control and an increased ability for a user to control the voltage output. A port 1210 is disposed on the housing 1100 and configured to receive a connector of a charging device to charge the power source and other electric components operably connected thereto. In the illustrated embodiment, the port is a USB charging port. However, in alternate embodiments, the port 1210 is any suitable configuration adapted to receive external power to supply to the portable vaporizer system 1000.

A power button 1310 is disposed on the exterior of the housing 1100 and configured to activate a control circuit of the system. In the illustrated embodiment, the power button 1310 is activated through a distinct series of depressions or movements depending on a method to be executed by a microprocessor disposed within the housing 1100. In the shown embodiment, the power button 1310 is the only activation button disposed on the housing 1100. In alternate embodiments, distinct buttons execute distinct functions of the microprocessor.

Figure 3:
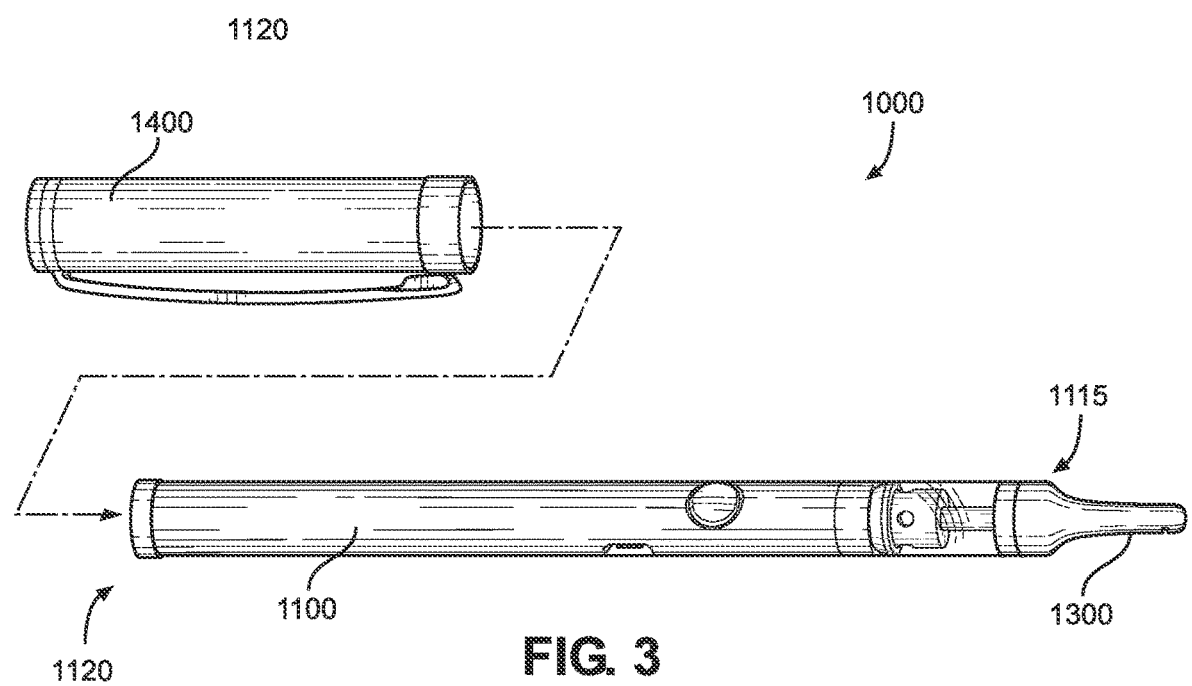
FIG. 3 shows a perspective view of an embodiment of the portable vaporizer system wherein the lid is detached therefrom.

Referring now to FIG. 3, there is shown a perspective view of an embodiment of the portable vaporizer system wherein the lid is detached therefrom. In the illustrated embodiment, a lid 1400 is removably securable to either the first end 1115 or the second end 1120 of the housing 1100. In the shown embodiment, the lid 1400 comprises a similar appearance to a pen cap, such that when the lid 1400 is secured to the first end 1115 of the housing 1100, the mouthpiece 1300 mounted to the first end is entirely concealed to allow a user to possess the system in a discrete manner. A securement clip extends from the lid 1400 to allow the housing 1100 to be secured to an article of clothing or accessory of the user. In the illustrated embodiment, the lid 1400 secures to the housing 110 via a friction fit. In operation, the user can secure the lid 1400 to the second end 1120 in order to prevent misplacing the lid 1400 when vaping.

In some embodiments (as illustrated in FIG. 2), the lid 1400 comprises a cleaner 1410 disposed on an interior thereof for cleaning the mouthpiece 1300. In the illustrated embodiment, the cleaner 1410 is a fabric or foam material, wherein the fabric or foam is configured to deform to the shape of the mouthpiece with the lid 1400 is attached to the housing 1100. The cleaner 1410 comprises a cylindrical shape having a channel that tapers towards a closed end of the lid 1400, wherein the channel is configured to receive the mouthpiece therein. In some embodiments, a disinfectant is embedded within the fabric or foam material. In operation, the lid 1400 is attached to the first end 1115 of the housing 110 and rotated or twisted so as to frictionally engage with and deform to the shape of the mouthpiece 1300. In this way, the cleaner 1410 serves to wipe off and in some embodiments disinfects the mouthpiece 1300 after each use.

Figure 4:
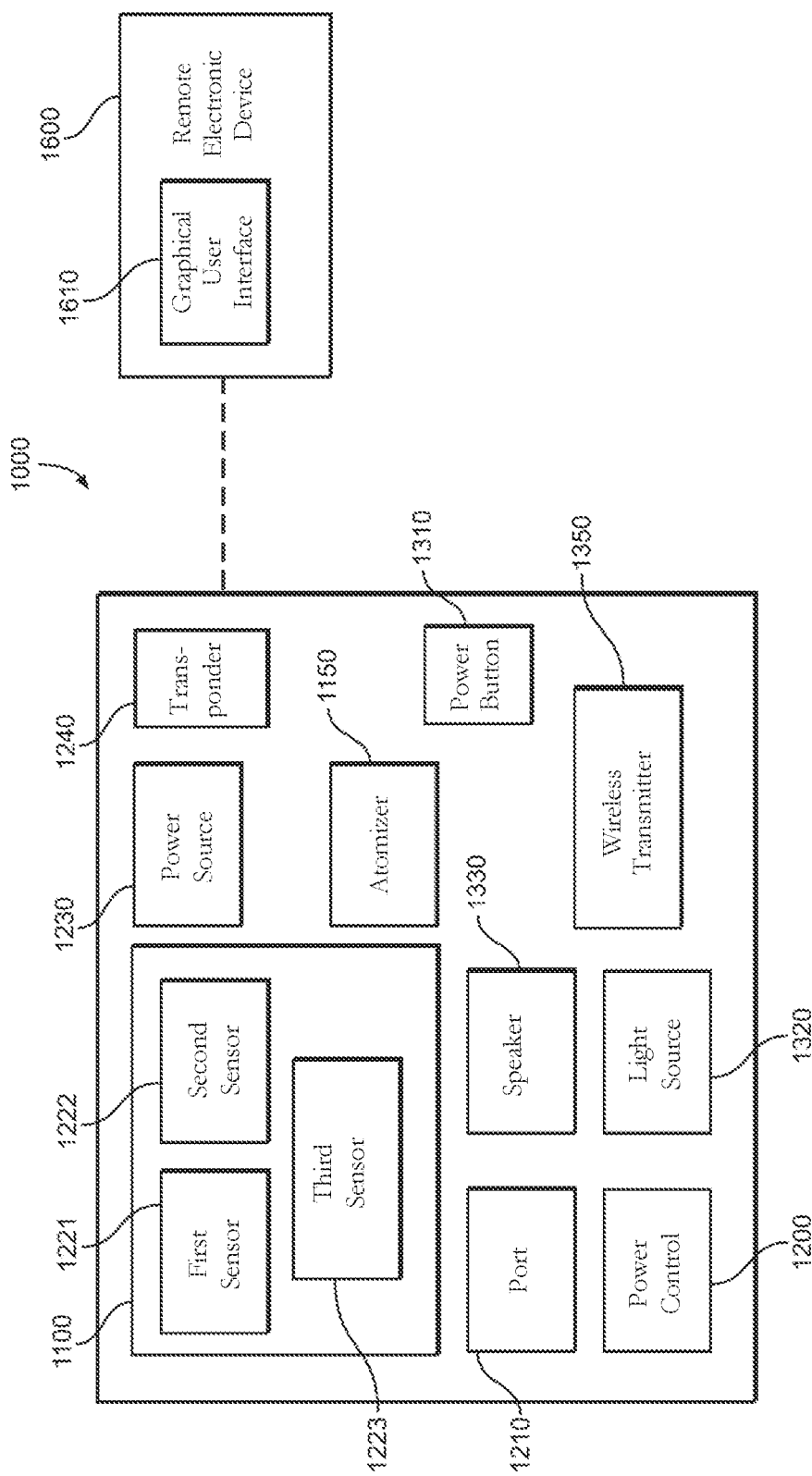
FIG. 4 shows a block diagram of a control circuit of an embodiment of the portable vaporizer system.

Referring now to FIG. 4, there is shown a block diagram of a control circuit of an embodiment of the portable vaporizer system. The power control 1200 is configured to selectively adjust voltage supplied from the power source 1230 to the atomizer 1150 for controlling a fluid temperature during the vaporizing process. In the illustrated embodiment, the power source is disposed within the second end 1120 of the housing 1100 and can be removed or replaced as needed. In the illustrated embodiment, the power source 1230 is a battery, such as a lithium or ion battery. However, any suitable power source can be used. The port 1210 is operably connected to the control circuit in order to charge the power source as needed.

A sensor 1220 is disposed within the housing 1100 for detecting the user data and usage of the portable vaporizer system 1000. In the illustrated embodiment, the housing 1100 comprises a first sensor 1221 configured to detect fluid levels within the fluid chamber. A second sensor 1222 is configured to detect power usage through measuring output of the power source 1230 and a third sensor 1223 is configured to detect flow rate of fluid passing through the airflow channel. In some embodiments, the first, second, and third sensors are combined into a multifunctional single sensor. In alternate embodiments, the sensors 1220 are distinct from one another and positioned in separate areas of the housing 1100. The information detected by the sensor is stored as user data on a non-transitory data storage module within the housing 1100.

The portable vaporizer system further comprises a wireless transmitter 1350, such as Bluetooth, configured to transmit the user data to a remote electronic device 1600. The remote electronic device 1600 is any computing device configured to receive and display information, such as a computer, smartphone, tablet, and the like. The remote electronic device 1600 comprises a graphical user interface (GUI) 1610 that displays the user data thereon. The GUI is configured to receive user input that associates a specific user with a specific housing. Thus, when the user input is recognized, the user data stored on the housing will be transmitted to the remote electronic device 1600 to be displayed on the GUI.

In other embodiments, the portable vaporizer system 1000 comprises a location module having a speaker 1330 and a light source 1320 configured to project an audible alert and illuminate, respectively, upon remote activation of the user. In the illustrated embodiment, the light source 1320 is a ring disposed entirely around a perimeter of the power button 1310. In some embodiments, the audible alert is a number of consecutive beeps or pings that continue until the user locates his or her housing 1100. In this way, a user can connect to the portable vaporizer system 1000 through the GUI and activate the location module in attempts in order to hear or see the housing. In some embodiments, the portable vaporizer system comprises a GPS transponder 1240 configured to transmit a location of the housing 1100 to the GUI 1610 of the electronic device 1600 associated with the user. Thus, when a user accesses the portable vaporizer system through the GUI, the location of the housing 1100 is configured to be displayed on a map on the GUI.

In one embodiment, the portable vaporizer method comprises providing the portable vaporizer system and detecting the user data through the sensors disposed in the housing. The power source is activated and deactivated by depressing the power button a first and second predetermined number of times, respectively. For example, when the power button is pressed five times, the light source will illuminate, and the system will be active. When the power button is again depressed five times, the power source will deactivate the system will shut off. In some embodiments, the user data is transmitted to a remote electronic device when the power button is depressed a third predetermined number of times. In other embodiments, the portable vaporizer system is voice activated, wherein the power button can be depressed, and the user can vocalize a command, such as "order refill" or "shut down."

In some embodiments, the sensor is configured to track the number of times the power button is pressed at a certain heat level. This measurement allows the microprocessor to determine when the fluid levels will be depleted and send a signal to the user through the GUI to order a fluid refill. In alternate embodiments, the signal will be sent to a third party, such as a manufacturer of vapor fluid. The signal containing information of the user data will activate an automatic order refill directly with the manufacturer to be sent to the user. In this way, a user does not need to keep track of when the fluid will be depleted, but instead, the fluid refills will be automatically sent to the user's mailing address by the manufacturer. In the illustrated embodiment, this is achieved through detection of fluid levels via the sensor, the microprocessor programmed to detect when fluids are low, and the transmitter automatically sending the user data to the third party manufacturer for fluid refill delivery.

In alternate methods, the user data is accessible by the user's healthcare provider through the GUI so as to allow the healthcare provider to monitor and advise the user on safe usage of the portable vaporizer system. The GUI is configured to display how many times the users vapes during a day, week, month, or year. Further, the system is configured to detect flow rate such that if a threshold flow rate is surpassed, the system will transmit user data and display a message on the GUI indicating that the user is over-inhaling.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A portable vaporizer system, comprising:
   a housing having a first end and a second end extending between a longitudinal axis, an air inlet, and a vapor outlet;
   an airflow channel in the housing fluidly connects the air inlet to the vapor outlet;
   an atomizer disposed in the housing between the air inlet and the vapor outlet;
   a fluid chamber operably connected to the atomizer;
   a power control disposed at the second end of the housing configured to adjust voltage supplied from a power source to the atomizer;
   a sensor configured to detect fluid levels within the fluid chamber, flow rates of fluid passing through the airflow channel, and power usage by measuring output of the power source;
   a non-transitory data storage module configured to store the user data;
   a microprocessor having a logic configured to transmit the user data to a remote electronic device via a wireless transmitter.

2. The portable vaporizer system of claim 1, wherein the housing comprises a power button and a port adapted to receive a connector to recharge the power source.

3. The portable vaporizer system of claim 2, wherein the power button provides a plurality of control options, wherein each control option is operated via a distinct movement sequence of the power button.

4. The portable vaporizer system of claim 2, wherein the sensor detects a number of times the power button is actuated and at each heat level.

5. The portable vaporizer system of claim 1, further comprising a graphical user interface displayed on the remote electronic device and configured to receive the user data, wherein the graphical user interface is configured to display the user data stored on the data storage module.

6. The portable vaporizer system of claim 5, wherein the graphical user interface is configured to display a message indicating if the flow rate of a vaporized fluid, exiting the fluid chamber, air inlet, or vapor outlet, exceeds a threshold level.

7. The portable vaporizer system of claim 1, wherein the wireless transmitter is configured to transmit the user data stored on the data storage module to an online marketplace for automatic reordering when fluid levels within the fluid chamber reach a predetermined level.

8. The portable vaporizer system of claim 1, wherein the wireless transmitter is configured to transmit the user data stored on the data storage module to a healthcare provider for monitoring.

9. The portable vaporizer system of claim 1, further comprising a mouthpiece disposed on the first end of the housing.

10. The portable vaporizer system of claim 1, further comprising a light source configured to illuminate an exterior of the housing.

11. The portable vaporizer system of claim 1, further comprising a lid securable to a first end and a second end of the housing, wherein a mouthpiece mounted to the first end is entirely concealed within the lid when the lid is secured to the first end.

12. The portable vaporizer system of claim 11, wherein the lid comprises a cleaner disposed along an interior thereof and configured to engage with and deform to a shape of the mouthpiece when the lid is secured to the first end of the housing.

13. The portable vaporizer system of claim 1, further comprising a Global Positioning System transponder configured to transmit a location of the housing to a graphical user interface of an electronic device associated with a user.

14. The portable vaporizer system of claim 1, further comprising a location module comprising a speaker and a light source configured to project an audible alert and illuminate, respectively, upon remote activation of a user.

15. A method for activating and charging a portable vaporizer system, comprising:
  providing a housing having:
    a first end and a second end extending between a longitudinal axis, an air inlet, and a vapor outlet;
    an airflow channel in the housing connecting the air inlet to the vapor outlet;
    an atomizer in the housing between the air inlet and the vapor outlet;
    a fluid chamber operably connected to the atomizer;
    a power control disposed at the second end of the housing configured to adjust voltage supplied from a power source to the atomizer;
    a sensor configured to detect fluid levels, flow rates, power usage;
    a non-transitory data storage module configured to store user data;
    a microprocessor having a logic configured to transmit the user data to a remote electronic device via a wireless transmitter;
  activating the power source when a power button is depressed a first predetermined number of times;
  storing and recording the user data;
  transmitting the user data to a remote electronic device when the power button is depressed a second predetermined number of times.

16. The method for activating and charging a portable vaporizer system of claim 15, further comprising:
  detecting a predetermined fluid levels via the sensor;
  transmitting an automated refill request to an online marketplace upon detection of the predetermined fluid level;
  receiving delivery of a liquid refill.

* * * * *